United States Patent [19]

Evans et al.

[11] Patent Number: 5,990,163
[45] Date of Patent: Nov. 23, 1999

[54] SELECTIVE MODULATION OF PROCESSES MEDIATED BY RETINOID X RECEPTORS, AND COMPOUNDS USEFUL THEREFOR

[75] Inventors: Ronald M. Evans, La Jolla, Calif.; David J. Mangelsdorf, Duncanville, Tex.; Richard A. Heyman, Encinitas; Marcus F. Boehm, San Diego, both of Calif.; Margaret A. Harmon, Irving, Tex.

[73] Assignee: The Salk Institute for Biological Studies, La Jolla, Calif.

[21] Appl. No.: 08/372,218

[22] Filed: Jan. 13, 1995

[51] Int. Cl.$^6$ .......................... A61K 31/20; A61K 31/23; A61K 31/335
[52] U.S. Cl. .......................... 514/549; 514/475; 514/560
[58] Field of Search .................................... 514/549, 560, 514/475

[56] References Cited

PUBLICATIONS

Akita et al. "Nonbleachable Rhodospins Retaining the Full Natural Chromophore" *J. Am. Chem. Soc.* 102:6372–6374 (1980).

Asato et al. "Retinal and Rhodospin Analogues Directed toward a Better Understanding of the H.T.–n Model of the Primary Process of Vision" *J. Am. Chem. Soc.* 108:5032–5033 (1986).

Boehm et al. "Synthesis and Structure–Activity Relationships of Novel Retinoid X Receptor–Selective Retinoids" *J. Med. Chem.* 37:2930–2941 (1994).

Brand et al. "Identification of a second human retinoic acid receptor" *Nature* 332:850–853 (1988).

Clayton and Goodwin "The Biological Significance of the Terpenoid Pathway of Biosynthesis" *Aspects of Terpenoid Chemistry and Biology*, Goodwin, ed. (Academic press, London) Chapter 1:1–23 (1971).

de Lera et al. "Synthesis and Studies of 12–S–CIS Conformationally Locked Retinoids" *Chemistry and Biology of Synthetic Retinoids,* Dawson and Okamura, eds., CRC Press, Inc., Chapter 9:202–227 (1990).

Derguini and Nakanishi "Synthetic rhodopsin analogs" *Photobiochem. and Photobiophys.* 13:259–283 (1986).

Giguere et al. "Identification of a receptor for the morphogen retinoic acid" *Nature* 330:624–629 (1987).

Heyman et al. "9–Cis Retinoic Acid Is a High Affinity Ligand for the Retinoid X Receptor" *Cell* 68:397–406 (1992).

Ishikawa et al. "A Functional Retinoic Acid Receptor Encoded by the Gene on Human Chromosome 12" *Mol. Endo.* 4:837–844 (1990).

Ito, M. "Synthesis and Application of Retinoids and Related Compounds to vision Research and Cancer Studies" *Chemistry and Biology of Synthetic Retinoids,* Dawson and Okamura, eds., CRC Press, Inc., Chapter 4:78–97 (1990).

Ladias and Karathanasis "Regulation of the apolipoprotein AI Gene by ARP–1, a Novel Member of the Steroid Receptor Superfamily" *Science* 251:561–565 (1991).

Mangelsdorf et al. "A Direct Repeat in the Cellular Retinol–Binding Protein Type II Gene Confers Differential Regulation by RXR and RAR" *Cell* 66:555–561 (1991).

Mangelsdorf et al. "Characterization of three RXR genes that mediate the action of 9–cis retinoic acid" *Genes and Development* 6:329–344 (1992).

Mangelsdorf et al. "Nuclear receptor that identifies a novel retinoic acid response pathway" *Nature* 345:224–229 (1990).

Mangelsdorf et al. "The Retinoid Receptors" *The Retinoids: Biology, Chemistry, and Medicine,* 2nd ed., edited by Sporn et al., (Raven Press, Ltd., New York), Chapter 8:319–349 (1994).

Miyajima et al. "Identification of two novel members of erbA superfamily by molecular cloning: the gene products of the two are highly related to each other" *Nucleic Acids Research* 16:11057–11074 (1988).

Mlodzik et al. "The Drosophila seven–up Gene, a Member of the Steroid Receptor Gene Superfamily, Controls Photoreceptor Cell Fates" *Cell* 60:211–224 (1990).

Oro et al. "Relationship between the product of the *Drosophila ultraspiracle* locus and the vertebrate retinoid X receptor" *Nature* 347:298–301 (1990).

Quistad et al. "Environmental Degradation of the Insect Growth Regulator Methoprene (Isopropyl (2E, 4E)–11–Methoxy–3,7,11–trimethyl–2,4–dodecadienoate).I.Metabolism by Alfalfa and Rice" *J. Agr. Food Chem.* 22:582–589 (1974).

Sadowski and Ptashne "A vector for expressing GAL4(1–147) fusions in mammalian cells" *Nucl. Acids Res.* 17:7539 (1989).

Sheves et al. "An Artificial Visual Pigment with Restricted $C_9$–$C_{11}$ Motion Forms Normal Photolysis Intermediates" *J. Am. Chem. Soc.* 108:6440–6441 (1986).

Sladek et al. "Liver–enriched transcription factor HNF–4 is a novel member of the steroid hormone receptor superfamily" *Genes & Development* 4:2353–2365 (1990).

Umesono et al. "Direct Repeats as Selective Response Elements for the Thyroid Hormone, Retinoic Acid, and Vitamin $D_3$ Receptors" *Cell* 65:1255–1266 (1991).

Unsworth et al. "Teratogenic Evaluation of Terpenoid Derivatves" *Life Sciences* 15:1649–1655 (1974).

Wang et al. "COUP transcription factor is a member of the steroid receptor superfamily" *Nature* 340:163–166 (1989).

Webster et al. "The Yeast $UAS_G$ Is a Transcriptional Enhancer in Human HeLa Cells in the Presence of the GAL4 Trans–Activator" *Cell* 52:169–178 (1988).

Wecksler and Normn "An Hydroxylapatite Batch Assay for the Quantitation of 1α,25–Dihydroxyvitamin $D_3$–Receptor Complexes" *Analytical Biochem.* 92:314–323 (1979).

*Primary Examiner*—Richard L. Raymond
*Attorney, Agent, or Firm*—Gray Cary Ware & Freidenrich; Stephen E. Reiter

[57] ABSTRACT

In accordance with the present invention, ligands have been discovered which selectively bind retinoid X receptors. Such ligands can be used for the selective modulation of retinoid X receptor mediated processes. In a further aspect of the present invention, there are provided pharmaceutical compositions comprising a pharmaceutically acceptable vehicle containing at least one of the above-described selective ligands. Such compositions are useful, for example, for the treatment of a variety of retinoid X receptor mediated disease states.

16 Claims, 4 Drawing Sheets

SEQUENCE LISTING

```
<160> NUMBER OF SEQ ID NOS: 1

<210> SEQ ID NO 1
<211> LENGTH: 71
<212> TYPE: PRT
<213> ORGANISM: Artificial Sequence
<220> FEATURE:
<223> OTHER INFORMATION: Nuclear/intracellular receptors
<220> FEATURE:
<221> NAME/KEY: VARIANT
<222> LOCATION: 7,9,11,13,22,27,62,65, 70
<223> OTHER INFORMATION: Residues that are almost universally conserved,
      but for which variations have been found in some
      identified hormone receptors <220> FEATURE:
<221> NAME/KEY: VARIANT
<222> LOCATION: (1)...(71)
<223> OTHER INFORMATION: Xaa = Non-conserved Amino Acids within the
      DNA-binding domain

<400> SEQUENCE: 1

Cys Xaa Xaa Cys Xaa Xaa Arg Xaa Ala Xaa Gly Xaa Tyr Xaa Xaa Xaa
 1               5                  10                  15

Xaa Cys Xaa Xaa Cys Lys Xaa Phe Phe Xaa Arg Xaa Xaa Xaa Xaa Xaa
            20                  25                  30

Xaa Xaa Xaa Xaa Xaa Xaa Cys Xaa Xaa Xaa Xaa Xaa Xaa Xaa Xaa Cys
```

-continued

```
          35                  40                  45
Xaa Xaa Xaa Lys Xaa Xaa Arg Xaa Xaa Cys Xaa Xaa Cys Arg Xaa Xaa
    50                  55                  60

Lys Cys Xaa Xaa Xaa Gly Met
65                  70
```

SELECTIVE MODULATION OF PROCESSES MEDIATED BY RETINOID X RECEPTORS, AND COMPOUNDS USEFUL THEREFOR

FIELD OF THE INVENTION

The present invention relates to intracellular receptors, and ligands therefor. In a particular aspect, the present invention, relates to methods for selectively modulating processes mediated by retinoid X receptors.

BACKGROUND OF THE INVENTION

A central focus of research in eukaryotic molecular biology continues to be the elucidation of molecules and mechanisms that mediate specific gene regulation in response to exogenous inducers such as hormones or growth factors. Indeed, a great deal of work has been done in efforts to identify exogenous inducers which are capable of mediating specific gene regulation.

Although much remains to be learned about the specifics of gene regulation, it is known that exogenous inducers modulate gene transcription by acting in concert with intracellular components, including intracellular receptors and discrete DNA sequences known as hormone response elements (HREs).

As additional members of the steroid/thyroid superfamily of receptors are identified, the search for exogenous inducers (i.e., naturally occurring (or synthetic) molecules) for such newly discovered receptors has become an important aspect of the ongoing effort to learn about the specifics of gene regulation.

The retinoid members of the steroid/thyroid superfamily of receptors, for example, are responsive to compounds referred to as retinoids, which include retinoic acid, retinol (vitamin A), and a series of natural and synthetic derivatives which have been found to exert profound effects on development and differentiation in a wide variety of systems.

Indeed, vitamin A metabolites (i.e. retinoids) have been determined to play essential roles in many aspects of development, metabolism and reproduction in vertebrates (see, for example, *The Retinoids*, Second Edition, Sporn et al. (Raven Press, New York, 1994)). There are two classes of retinoid receptors: the retinoic acid receptors (RARs), which bind to both all-trans retinoic acid (atRA) and 9-cis retinoic acid (9cRA), and the retinoid X receptors (RXRs), which bind only to 9cRA. These receptors modulate ligand-dependent gene expression by interacting as RXR/RAR heterodimers or RXR homodimers on specific target gene DNA sequences known as hormone response elements. In addition to their role in retinoid signalling, RXRs also serve as heterodimeric partners of nuclear receptors for vitamin D, thyroid hormone, and peroxisome proliferators (reviewed by Mangelsdorf et al., at pages 319–349 of *The Retinoids*, Second Edition, Sporn et al. (Raven Press, New York, 1994)).

The identification of additional compounds which interact with retinoid receptors, and thereby affect transcription of genes which are responsive to retinoic acid (or other metabolites of vitamin A), would be of significant value, e.g., for therapeutic applications.

Although both RAR and RXR respond to retinoic acid in vivo, the receptors differ in several important aspects. First, RAR and RXR are significantly divergent in primary structure (e.g., the ligand binding domains of RARα and RXRα have only 27% amino acid identity). These structural differences are reflected in different relative degrees of responsiveness of RAR and RXR to various vitamin A metabolites and synthetic retinoids. In addition, distinctly different patterns of tissue distribution are seen for RAR and RXR. In contrast to the RARs, which are not expressed at high levels in the visceral tissues, RXRα mRNA has been shown to be most abundant in the liver, kidney, lung, muscle and intestine. Finally, response elements have recently been identified in the cellular retinol binding protein type II (CRBPII) and apolipoprotein AI genes which confer responsiveness to RXR, but not RAR. Indeed, RAR has also been recently shown to repress RXR-mediated activation through the CRBPII RXR response element. These data, in conjunction with the observation that both RAR and RXR can activate through the RAR response element of the RARβ promoter, indicate that the two retinoic acid responsive pathways are not simply redundant, but instead manifest a complex interplay.

In view of the related, but clearly distinct nature of these receptors, the identification of ligands which are selective for retinoid X receptor(s), relative to retinoic acid receptor (s), would be of great value in selectively controlling processes mediated by one or both of these retinoid receptor types.

BRIEF DESCRIPTION OF THE INVENTION

In accordance with the present invention, we have discovered ligands which selectively bind retinoid X receptors. Such ligands can be used for the selective modulation of retinoid X receptor mediated processes.

In a further aspect of the present invention, there are provided pharmaceutical compositions comprising a pharmaceutically acceptable vehicle containing at least one of the above-described selective ligands. Such compositions are useful, for example, for the treatment of a variety of retinoid X receptor mediated disease states.

DETAILED DESCRIPTION OF THE INVENTION

Figure 1:
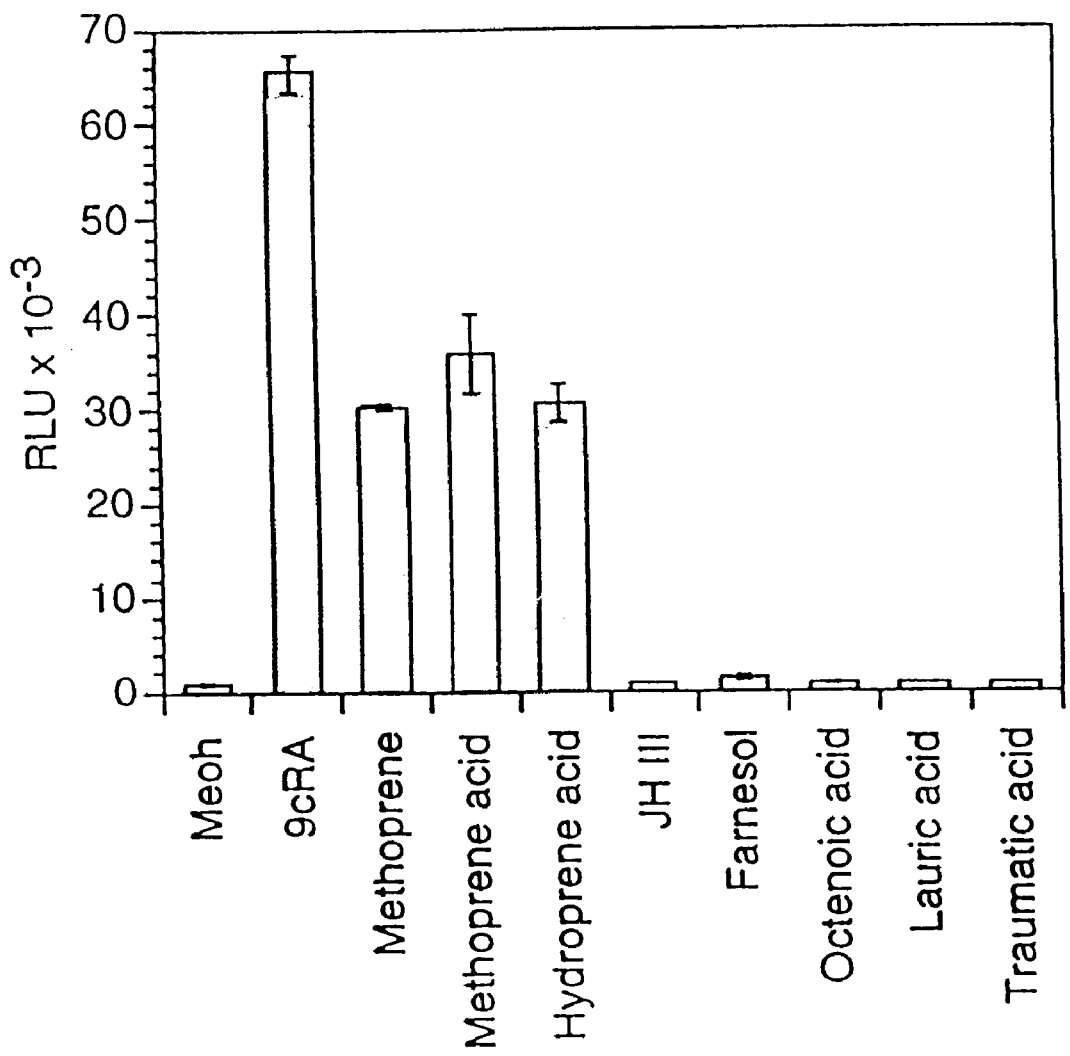
FIG. 1 summarizes the ability of various agents to activate RXR. Meoh refers to methanol, used as a solvent control. 9cRA refers to 9-cis-retinoic acid and JH III refers to juvenile hormone.

In accordance with the present invention, there are provided methods for selectively modulating process (es) mediated by retinoid X receptors, said method comprising conducting said process (es) in the presence of at least one compound of the structure:

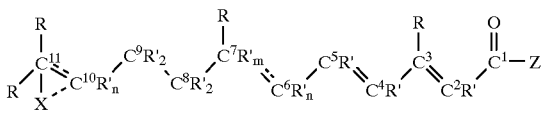

wherein:
  each R is independently selected from hydrogen, a straight chain, branched chain or cyclic alkyl moiety having 1 up to 6 carbon atoms, halide or a halo-substituted alkyl moiety;
  each R' is independently selected from hydrogen, straight or branched chain alkyl having 1 up to 4 carbon atoms, halide or a halo-substituted alkyl moiety;
  X is selected from hydrogen, a straight chain, branched chain or cyclic alkyl moiety having 1 up to 6 carbon atoms, —OR", wherein R" is selected from hydrogen, a straight chain, branched chain or cyclic alkyl moiety having 1 up to 6 carbon atoms, —O— (thereby forming an epoxide ring bridging $C^{10}$ and $C^{11}$), —$CR''_2$— (thereby forming a cyclopropyl ring including X, $C^{10}$ and $C^{11}$); or X is absent when there is a double bond between $C^{10}$ and $C^{11}$;
  Z is selected from hydrogen, a straight chain, branched chain or cyclic alkyl moiety having 1 up to 6 carbon atoms, —OR" or —$NR''_2$, wherein each R" is independently as defined above;
  m is 0 when there is a double bond between $C^6$ and $C^7$, or m is 1 when there is a single bond between $C^6$ and $C^7$; and
  each n is 1 when there is a double bond between $C^6$ and $C^7$, and/or between $C^{10}$ and $C^{11}$, or each n is 2 when there is a single bond between $C^6$ and $C^7$, and/or between $C^{10}$ and $C^{11}$.

Exemplary R groups include hydrogen, methyl, ethyl, propyl, isopropyl, n-butyl, isobutyl, t-butyl, n-pentyl, neopentyl, n-hexyl, cyclohexyl, trifluoromethyl, fluorine, chlorine, bromine, and the like; exemplary R' groups include hydrogen, methyl, ethyl, propyl, isopropyl, n-butyl, isobutyl, t-butyl, trifluoromethyl, fluorine, chlorine, bromine, and the like; exemplary R" groups include hydrogen, methyl, ethyl, propyl, isopropyl, n-butyl, t-butyl, and the like; exemplary X groups include hydrogen, methyl, ethyl, propyl, isopropyl, n-butyl, t-butyl, pentyl, neopentyl, n-hexyl, cyclohexyl, hydroxy, methoxy, ethoxy, propoxy, butoxy, and the like; and exemplary Z groups include hydrogen, methyl, ethyl, propyl, butyl, pentyl, hexyl, cyclohexyl, hydroxy, methoxy, ethoxy, propoxy, butoxy, amino, methylamino, dimethylamino, ethylamino, diethylamino, propylamino, dipropylamino, and the like.

Presently preferred compounds for use in the practice of the present invention are those wherein:
  the backbone is a 2,4-dodecadiene (preferably 2E,4E configuration), each R is methyl, each R' is hydrogen, X is methoxy, Z is —$OCH_2(CH_3)_2$, m=1 and each n=2, or
  the backbone is a 2,4-dodecadiene (preferably 2E,4E configuration), each R is methyl, each R' is hydrogen, X is methoxy, Z is —OH, m=1 and each n=2, or
  the backbone is a 2,4,6,10-dodecatetraene, (preferably 2E,4E,6E configuration), each R is methyl, each R' is hydrogen, X is methoxy, Z is —$OCH_2(CH_3)_2$, m=0 and each n=1, or
  the backbone is a 2,4,6,10-dodecatetraene, (preferably 2E,4E,6E configuration), each R is methyl, each R' is hydrogen, X is methoxy, Z is —OH, m=0 and each n=1, or the like.

As employed herein, the term "modulate" refers to the ability of a ligand for a member of the steroid/thyroid superfamily to induce expression of target gene(s), or to repress expression of target gene(s).

As employed herein, the phrase "processes mediated by retinoid X receptors" refers to biological, physiological, endocrinological, and other bodily processes which are mediated by receptor or receptor combinations which are responsive to natural or synthetic retinoids, or natural or synthetic compounds as defined herein (referred to herein as "rexoids" because of the ability of the compounds described herein to selectively activate retinoid X receptors). Modulation of such processes can be accomplished in vitro or in vivo. In vivo modulation can be carried out in a wide range of subjects, such as, for example, humans, rodents, sheep, pigs, cows, and the like.

Exemplary receptors which are responsive to retinoids, and natural or synthetic compounds as defined herein (i.e., "rexoids") include retinoid X receptor-alpha, retinoid X receptor-beta, retinoid X receptor-gamma, and splice variants encoded by the genes for such receptors; as well as various combinations thereof (i.e., homodimers, homotrimers, heterodimers, heterotrimers, and the like), including combinations of such receptors with other members of the steroid/thyroid superfamily of receptors with which the retinoid X receptors may interact by forming heterodimers, heterotrimers, and higher heteromultimers. For example, the retinoic acid receptor-alpha may form a heterodimer with retinoid X receptor-alpha, the retinoic acid receptor-beta may form a heterodimer with retinoid X receptor-alpha, retinoic acid receptor-gamma may form a heterodimer with retinoid X receptor-alpha, retinoid X receptor-alpha may form a heterodimer with thyroid receptor, retinoid X receptor-beta may form a heterodimer with vitamin D receptor, retinoid X receptor-gamma may form a heterodimer with retinoic acid receptor-alpha, and the like.

As employed herein, the phrase "members of the steroid/thyroid superfamily of receptors" (also known as "nuclear receptors" or "intracellular receptors") refers to hormone binding proteins that operate as ligand-dependent transcription factors, including identified members of the steroid/thyroid superfamily of receptors for which specific ligands have not yet been identified (referred to hereinafter as "orphan receptors"). These hormone binding proteins have the intrinsic ability to bind to specific DNA sequences. Following binding, the transcriptional activity of target gene (i.e., a gene associated with the specific DNA sequence) is modulated as a function of the ligand bound to the receptor.

The DNA-binding domains of all of these nuclear receptors are related, consisting of 66–68 amino acid residues, and possessing about 20 invariant amino acid residues, including nine cysteines.

A member of the superfamily can be identified as a protein which contains the above-mentioned invariant amino acid residues, which are part of the DNA-binding domain of such known steroid receptors as the human glucocorticoid receptor (amino acids 421–486), the estrogen receptor (amino acids 185–250), the mineralocorticoid receptor (amino acids 603–668), the human retinoic acid receptor (amino acids 88–153). The highly conserved amino acids of the DNA-binding domain of members of the superfamily are as follows:

```
Cys-X-X-Cys-X-X-Asp*-X-                (SEQ ID NO 1)
Ala*-X-Gly*-X-Tyr*-X-X-
X-X-Cys-X-X-Cys-Lys*-
X-Phe-Phe-X-Arg*-X-X-X-
X-X-X-X-X-(X-X-)Cys-
X-X-X-X-X-(X-X-X-)Cys-
X-X-X-Lys-X-X-Arg-X-X-
Cys-X-X-Cys-Arg*-X-X-
Lys*-Cys-X-X-X-Gly*-Met;
``` wherein X designates non-conserved amino acids within the DNA-binding domain; the amino acid residues denoted with an asterisk are residues that are almost universally conserved, but for which variations have been found in some identified hormone receptors; and the residues enclosed in parenthesis are optional residues (thus, the DNA-binding domain is a minimum of 66 amino acids in length, but can contain several additional residues).

Exemplary members of the steroid/thyroid superfamily of receptors include steroid receptors such as glucocorticoid receptor, mineralocorticoid receptor, progesterone receptor, androgen receptor, vitamin $D_3$ receptor, and the like; plus retinoid receptors, such as RARα, RARβ, RARγ, and the like, plus RXRα, RXRβ, RXRγ, and the like; thyroid receptors, such as TRα, TRγ, and the like; as well as other gene products which, by their structure and properties, are considered to be members of the superfamily, as defined hereinabove. Examples of orphan receptors include HNF4 [see, for example, Sladek et al., in *Genes & Development* 4: 2353–2365 (1990)], the COUP family of receptors [see, for example, Miyajima et al., in *Nucleic Acids Research* 16: 11057–11074 (1988), Wang et al., in *Nature* 340: 163–166 (1989)], COUP-like receptors and COUP homologs, such as those described by Mlodzik et al., in *Cell* 60: 211–224 (1990) and Ladias et al., in *Science* 251: 561–565 (1991), the ultraspiracle receptor [see, for example, Oro et al., in *Nature* 347: 298–301 (1990)], and the like.

Processes capable of being modulated by retinoid X receptors, in accordance with the present invention, include in vitro cellular differentiation (e.g., in vitro differentiation of mouse teratocarcinoma cells (F9 cells), in vitro differentiation of human epidermal keratinocytes, and the like), in vitro cellular proliferation (e.g., in vitro proliferation of melanoma cell lines, and the like), limb morphogenesis, regulation of cellular retinal binding protein (CRBP), and the like. As readily recognized by those of skill in the art, the availability of selective ligands for the retinoid X receptor makes it possible, for the first time, to carry out assays for the identification of antagonists for such receptors.

Processes capable of being modulated by retinoid X receptors, in accordance with the present invention, also include the in vivo modulation of lipid metabolism, in vivo modulation of skin-related processes (e.g., acne, aging, wrinkling, skin cancer, and the like), in vivo modulation of malignant cell development, such as occurs, for example, in acute promyelocytic leukemia, testicular cancer, lung cancer, and the like. The ability of compounds of the invention to modulate such processes is evidenced in a number of ways. For example, RXR-alpha, in the presence of ligand therefor (e.g., methoprene acid) has been shown to exert a strong effect on the expression of genes under the control of regulatory elements of apolipoprotein AI. Similarly, studies with model systems for a variety of disease states (e.g., differentiation of HL60 cells as a model for acute promyelocytic leukemia, proliferation of melanoma cell lines as a model for skin cancer, differentiation of keratinocytes as a model for nonmalignant skin disorders, and the like) demonstrate the utility of retinoid X receptors, in the presence of ligand therefor, e.g., methoprene acid, for the treatment of such disease states. Such in vivo applications of the invention process may allow the modulation of various biological processes with reduced occurrence of undesirable side effects, and the like.

In vivo applications of the invention process (es) (and compositions) can be employed with a wide range of subjects, such as, for example, humans, rodents, sheep, pigs, cows, and the like.

"Rexoid" derivatives as described herein can be prepared employing a variety of synthetic methods, which are readily available (and well known) to those of skill in the art. See, for example, the methods described in *Chemistry and Biology of Synthetic Retinoids*, Dawson and Okamura, eds., CRC Press, Inc. (1990), especially Chapter 4, by Ito (found at pages 78–97), and Chapter 9, by de Lera et al. (found at pages 202–227) can readily be adapted for the preparation of the compounds described herein. The contents of this publication are hereby incorporated by reference herein. See also Asato et al., *J. Am. Chem. Soc.* 108: 5032 (1986); Sheves et al., *J. Am. Chem. Soc.* 108: 6440 (1986); Akita et al., *J. Am. Chem. Soc.* 102: 6370 (1980); Derguini and Nakanishi, *Photobiochem.* and *Photobiophys.* 13: 259 (1986), the entire contents of each of which is hereby incorporated by reference herein.

In accordance with another embodiment of the present invention, there are provided novel compositions comprising rexoid compound(s) as described herein (e.g., methoprene, methoprene acid, and the like) in a pharmaceutically acceptable vehicle. Examples of such compounds include methoprene, methoprene acid, and the like, as described hereinabove.

The invention compounds can be employed for both in vitro and in vivo applications. For in vivo applications, the invention compounds can be incorporated into a pharmaceutically acceptable formulation for administration. Those of skill in the art can readily determine suitable dosage levels when the invention compounds are so used.

As employed herein, the phrase "suitable dosage levels" refers to levels of compound sufficient to provide circulating concentrations high enough to effect activation of retinoid receptor(s). Such a concentration typically falls in the range of about 10 nM up to 2 $\mu$M; with concentrations in the range of about 100 nM up to 200 nM being preferred.

In accordance with a particular embodiment of the present invention, compositions comprising at least one 9-cis-retinoic acid-like compound (as described above), and a pharmaceutically acceptable carrier are contemplated. Exemplary pharmaceutically acceptable carriers include carriers suitable for oral, intravenous, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use.

The invention will now be described in greater detail by reference to the following non-limiting examples.

EXAMPLE 1
Identification of Compound(s) that Activate RXR

As part of an ongoing search for new RXR ligands, several sources of natural and synthetic compounds were screened utilizing a cotransfection assay similar to that described by Mangelsdorf et al., in *Genes and Development* 6:329 (1992) and Heyman et al., in *Cell* 68:397 (1992).

Candidate ligands were initially tested in Schneider cells cotransfected with an RXR expression plasmid and a luciferase reporter plasmid containing an RXR specific response element. This reporter plasmid contains a minimal promoter and the hormone response element from the rat cellular retinol binding protein II gene (CRBPII), which can be activated by RXR, but not by RAR (see Mangelsdorf et al., in *Cell* 66:555 (1991)).

Thus, Schneider cells were cotransfected with the expression plasmid A5C-hRXRα (see Mangelsdorf et al., in *Nature* 354:224 (1990)), the luciferase reporter plasmid ADH-CRBPII-LUC (see Mangelsdorf et al., in *Genes and Development* 6:329 (1992)) and then incubated with methanol as a solvent control, or with the compounds indicated in FIG. 1.

Cell lysates were then assayed for luciferase activity, which is expressed as relative light units (RLU) and represents the mean of triplicate assays (±SEM) normalized to β-galactosidase as an internal control. Thus, Schneider cells in 6-well culture plates were co-transfected with 0.5 μg ADH-CRBPII-LUC, 0.5 μg A5C-βgal and 1 μg of receptor plasmid (either A5C-mRXRα, A5C-mRXRβ, A5C-mRXRγ or A5C-hRXRα) by the $CaPO_4$ precipitation method, as described by Heyman et al., in *Cell* 68:397 (1992) and Clayton in *Aspects of Terpenoid Chemistry and Biology*, T. W. Goodwin, ed. (Academic Press, London) pp. 1–23 (1971). After 24 hours, ligand was added to the transfected cells. Thirty six hours later, the cells were harvested and extracts prepared and assayed for enzyme activity as described by Heyman et al., supra, and Clayton, supra. Luciferase values were normalized for transfection and harvesting efficiency by measuring β-galactosidase activity, and the results reported as average relative light units (RLU) for at least two replicates.

FIG. 1 shows that transcription from the reporter construct was activated by 9-cis-retinoic acid (9cRA) and several analogues of juvenile hormone (JH), including methoprene, hydroprene, and derivatives thereof, i.e., methoprene acid and hydroprene acid. Indeed, inductions by RXR activators above methanol control were 175-fold for $10^{-5}M$ 9cRA, 80-fold for $10^{-4}M$ methoprene, 95fold for $10^{-5}M$ methoprene acid, and 81-fold for $10^{-4}M$ hydroprene acid.

Although methoprene (isopropyl (2E,4E)-11-methoxy-3,7,11-trimethyl-2,4-dodecadienoate) and hydroprene (ethyl (2E,4E)-3,7,11-trimethyl-2,4-dodecadienoate) activate RXR and are known for their potent JH-like activity in insects, the closely related compounds JH III (methyl (2E,6E)-10,11-epoxy-3,7,11-trimethyl-2,6dodecadienoate) and the JH-active isoprenoid farnesol (2E,6E,10E)-3,7,11-trimethyl-2,6,10-dodecatrienol) do not activate RXR in this assay. Chemically similar carbon chain fatty acids also are inactive.

EXAMPLE 2
Competitive Binding Studies

The results presented in Example 1 indicate that RXR can respond to both the ester and acid forms of certain JH analogues. To determine which of these compounds may be true RXR ligands, competitive ligand binding experiments were performed.

Thus, competition for 9cRA binding to RXRα by methoprene acid was accomplished by incubating human RXRα protein with 40 nM [$^3$H]9cRA in the presence of increasing concentrations of unlabelled methoprene acid. Binding analysis was performed as described by Boehm et al., in *J. Med. Chem.* 37:2930–2941 (1994). Compounds used in these studies were prepared according to Wecksler and Norman (*Anal. Biochem.* 92:314–323 (1979)).

Specific binding is expressed as percent tritium bound to RXRα, where 100% is the amount of specific 9cRA binding in the absence of methoprene acid. In contrast to methoprene acid, methoprene was unable to displace 9cRA binding at any concentration. Likewise, hydroprene acid, but not hydroprene, was observed to bind RXR.

Figure 2:
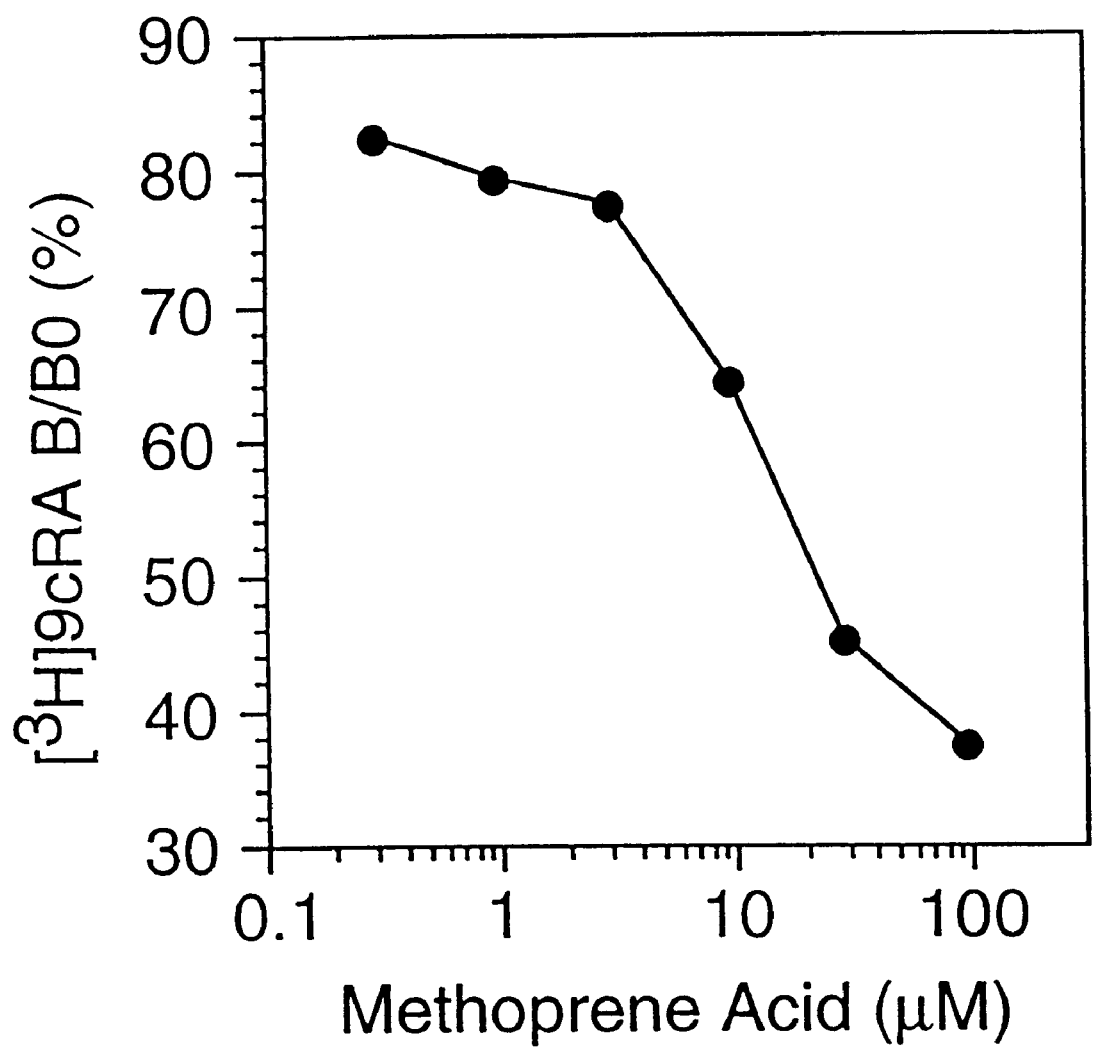
FIG. 2 demonstrates the ability of methoprene acid to bind RXR.

As shown in FIG. 2, methoprene acid competes well for [$^3$H]-9cRA binding to RXRα, demonstrating that the acid derivative is a direct RXR ligand. In contrast, methoprene is unable to competitively bind RXR at any concentration. These studies suggest that, in cells, methoprene is metabolically converted to the active form, i.e., methoprene acid. This hypothesis is supported by previous studies that have shown methoprene is metabolized within cells to several products, one of the major forms of which is the acid derivative, methoprene acid (see, for example, Quistad et al., in *J. Agr. Food Chem.* 22:582 (1974)). Esterases that may facilitate this conversion are found in many cell types; tissues which display high levels of esterase activity include the pancreas, liver and macrophages.

EXAMPLE 3
Transactivation Studies

Figure 3A:
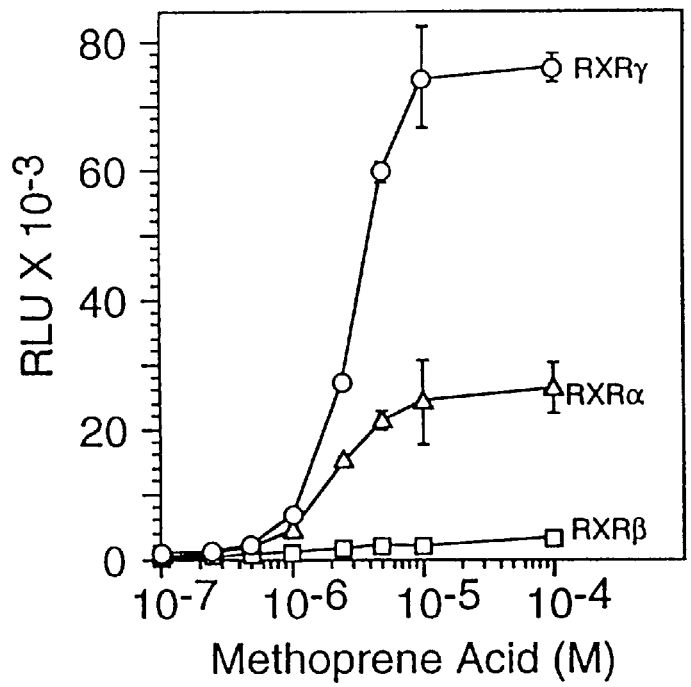
FIG. 3A presents dose response curves (generated with transfected insect Schneider cells) which demonstrate that methoprene acid is a ligand activator for all three known isoforms of RXR.
Figure 3B:
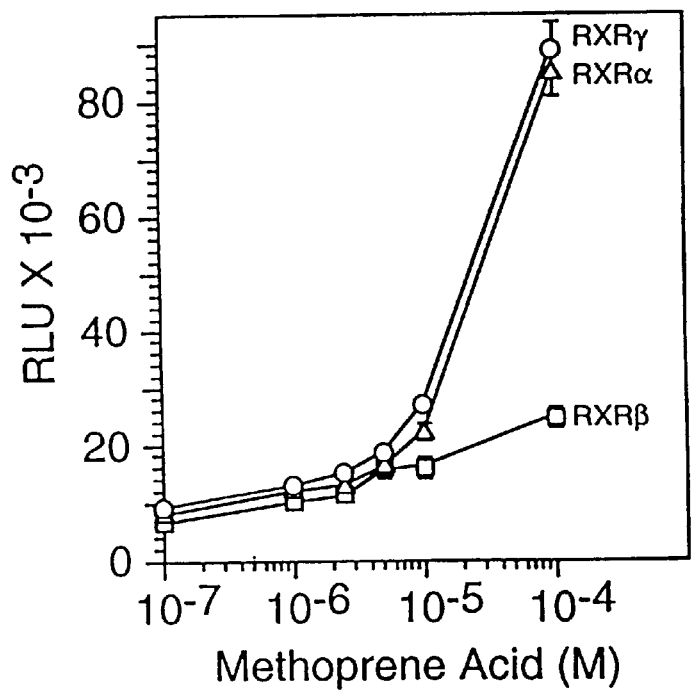
FIG. 3B presents dose response curves (generated with transfected mammalian CV-1 cells) which demonstrate that methoprene acid is a ligand activator for all three known isoforms of RXR.

To further test the ability of methoprene acid to function as an RXR ligand, the transactivation properties of methoprene on all three RXR subtypes was investigated. FIG. 3 presents the dose responses of the three RXR subtypes to methoprene acid in insect Schneider cells (FIG. 3A), or mammalian CV-1 cells (FIG. 3B) cotransfected with expression plasmids for mouse RXRα, RXRβ, or RXRγ and the reporter plasmid ADH-CRBPII-LUC (for Schneider cells) or TK-CRBPII-LUC (for CV-1 cells).

Experiments in Schneider cells were conducted as described in Example 1. Experiments in CV-1 cells were conducted as follows. CV-1 cells were seeded into 48-well sulture dishes and co-transfected with 50 ng of TK-CRBPII-LUC reporter plasmid, 50 ng of CMX-βgal expression plasmid, and 25 ng of expression plasmid for receptor (either CMX-mRXRα, CMX-mRXRβ or CMX-mRXRγ) by the $CaPO_4$ precipitation method, as described by Heyman et al., supra and Clayton supra. After eight hours, the precipitate was washed off of the cells with phosphate buffered saline (PBS), and media containing the appropriate concentration of putative ligand was placed over the cells. Luciferase activity was determined as described by Unsworth et al., in *Life Sciences* 15:1649 (1974).

As shown in FIG. 3, methoprene acid transactivates RXR in both insect Schneider cells and in mammalian CV-1 cells. The dose response for methoprene acid on each of the three RXR subtypes demonstrates a difference in maximal response, but approximately the same $ED_{50}$ for each of the receptors (compare FIGS. 3A and B). Similar to the effects seen with 9cRA (see Mangelsdorf et al., in *Genes and Development* 6:329 (1992)), RXRα and RXRγ respond strongly, whereas RXRβ responds only weakly to methoprene acid.

EXAMPLE 4
Co-transfection Experiments with Chimeric Receptors

Figure 4:
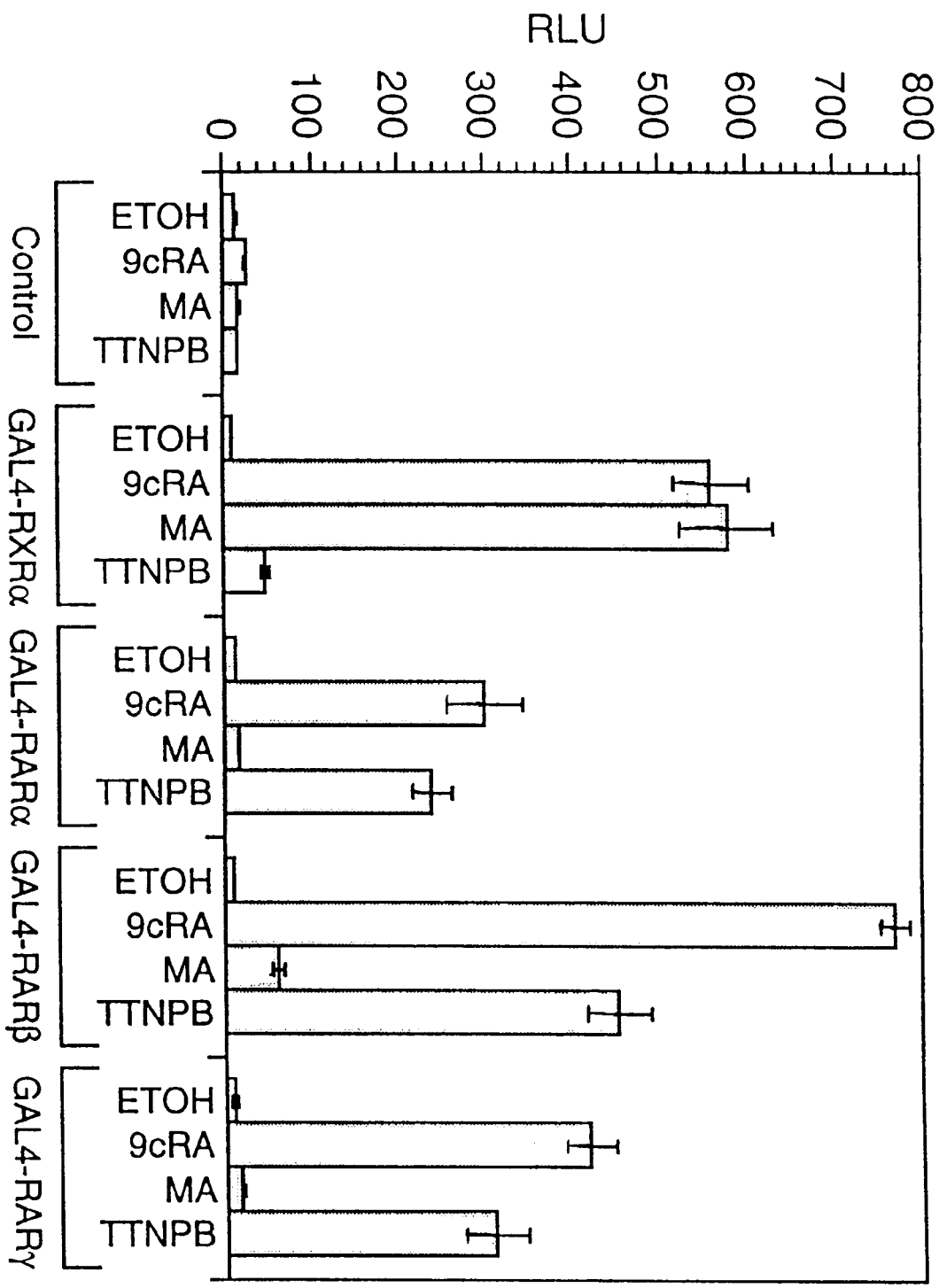
FIG. 4 demonstrates that methoprene acid is an RXR-specific ligand. Compounds tested include ethanol (ETOH), 9-cis-retinoic acid (9cRA), methoprene acid (MA), or the RAR-selective ligand (E)-4-[2-(5,6,7,8-tetrahydro-5,5,8,8-tetramethyl-2-napthalenyl)-1-propenyl]benzoic acid (TTNPB; see Mangelsdorf et al. in *Nature* 345:224 (1990)).

To demonstrate that the action of methoprene acid is specific for RXR, cotransfection experiments were performed using chimeric receptors in which the GAL4 DNA binding domain was fused to the ligand binding domains of either RXR or the three RAR subtypes (FIG. 4).

Thus, CV-1 cells were cotransfected with the expression plasmid CMX-GAL4-hRXRα, CMX-GAL4-hRARα, CMX-GAL4-RARβ or CMX-GAL4-RARγ and the reporter plasmid TK-MH100×4-LUC. The constructs consisted of the GAL4 DNA binding domain (amino acids 1–147; see Sadowski and Ptashne in *Nucl. Acids Res.* 17:7539 (1989)) ligated in frame to the ligand binding and C-terminal activation domains of hRARα (amino acids 203–462; see Giguere et al., in *Nature* 330:624 (1987), hRARβ (amino acids 178–448; see Brand et al., in *Nature* 332:850 (1988), RARγ (amino acids 187–454; see Ishikawa et al., in *Mol. Endo.* 4:837 (1990) and RXRα (amino acids 203–462; see Mangelsdorf et al., in *Nature* 345:224 (1990). These GAL4-receptor chimeras were then introduced into CMX expression vectors (see Umesono et al., in *Cell* 65:1255 (1991)). The GAL4-responsive reporter plasmid, TK-MH100×4-LUC, was constructed by inserting 4 copies of the yeast $UAS_G$ enhancer (i.e., MH100; see Webster et al., in *Cell* 52:169 (1988)) into the luciferase reporter plasmid TK-LUC. CV-1 cells seeded into 48 well culture plates were co-transfected with 80 ng of the reporter plasmid TK-Mh100×4-LUC, 50 ng of CMX-βgal expression plasmid, and 80 ng of receptor expression plasmid (either CMX-GAL4 as a control, CMX-GAL4-hRARα, CMX-GAL4-hRARβ, CMX-GAL4-hRARγ or CMX-GAL4-hRXRα). Cells were then incubated with $10^{-5}$M 9cRA, methoprene acid (MA), or the RAR-selective ligand TTNPB (see Mangelsdorf et al., *Nature* 354:224 (1990)). Cotransfections, ligand addition and luciferase assays were performed as described in Example 3.

The above-described chimeric proteins can bind to a GAL4 upstream activation sequence ($UAS_G$) in the promoter of a luciferase reporter, but can only activate transcription in the presence of the hybrid receptor's ligand. The distinct advantage of using the GAL4-receptor system, instead of the wild-type receptors and response elements, is that the GAL4-hybrids provide a sensitive and effective means for assaying receptor/ligand interactions, even in the presence of the cell's endogenous wild-type receptors.

The results presented in FIG. 4 demonstrate that, as expected, 9cRA can activate transcription with GAL4-RXR and all three of the GAL4-RAR subtypes. The specificity of the RAR subtypes is further shown by their exclusive response to the synthetic retinoid, TTNPB, which has previously been shown to be an RAR-selective ligand (see Mangelsdorf et al. in *Nature* 345:224 (1990)). In contrast, methoprene acid is specific for activation of only the GAL4-RXR.

While the invention has been described in detail with reference to certain preferred embodiments thereof, it will be understood that modifications and variations are within the spirit and scope of that which is described and claimed.

That which is claimed is:

1. A method for selectively modulating process(es) mediated by retinoid X receptors, said method comprising conducting said process(es) in the presence of at least one compound of the structure:

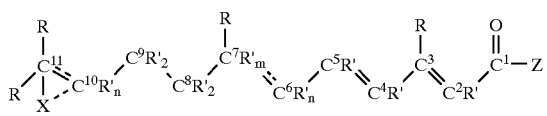

wherein:
each R is independently selected from hydrogen, or a straight chain or branched chain alkyl moiety having 1 up to 6 carbon atoms;
each R' is independently selected from hydrogen, or straight or branched chain alkyl having 1 up to 4 carbon atoms;
X is —OR", wherein R" is selected from hydrogen, a straight chain or branched chain alkyl moiety having 1 up to 6 carbon atoms, or —O—;
Z is —OR", wherein R" is as defined above;
m is 0 when there is a double bond between $C^6$ and $C^7$, or m is 1 when there is a single bond between $C^6$ and $C^7$; and
each n is 1 when there is a double bond between $C^6$ and $C^7$, and/or between $C^{10}$ and $C^{11}$, or each n is 2 when there is a single bond between $C^6$ and $C^7$, and/or between $C^{10}$ and $C^{11}$, wherein said process is modulated by said compound.

2. A method according to claim 1 wherein said retinoid X receptor is selected from retinoid X receptor-alpha, retinoid X receptor-beta, or retinoid X receptor-gamma.

3. A method according to claim 1 wherein the backbone of said compound is a 2,4-dodecadiene, each R is methyl, each R' is hydrogen, X is methoxy, Z is —OCH$_2$(CH$_3$)$_2$, m=1 and each n=2.

4. A method according to claim 1 wherein the backbone of said compound is a 2,4-dodecadiene, each R is methyl, each R' is hydrogen, X is methoxy, Z is —OH, m=1 and each n=2.

5. A method according to claim 1 wherein the backbone of said compound is a 2,4,6,10-dodecatetraene, each R is methyl, each R' is hydrogen, X is methoxy, Z is —OCH$_2$(CH$_3$)$_2$, m=0 and each n=1.

6. A method according to claim 1 wherein the backbone of said compound is a 2,4,6,10-dodecatetraene, each R is methyl, each R' is hydrogen, X is methoxy, Z is —OH, m=0 and each n=1.

7. A method according to claim 1 wherein said process is selected from in vitro cellular differentiation, in vitro cellular proliferation, regulation of cellular retinal binding protein (CRBP), or in vitro limb morphogenesis.

8. A method according to claim 7 wherein said in vitro cellular differentiation is selected from in vitro differentiation of mouse teratocarcinoma cells (F9 cells) or in vitro differentiation of human epidermal keratinocytes.

9. A method according to claim 7 wherein said in vitro cellular proliferation is in vitro proliferation of melanoma cell lines.

10. A method according to claim 1 wherein said process is selected from the in vivo modulation of lipid metabolism, in vivo modulation of skin-related processes, or in vivo modulation of malignant cell development.

11. A method according to claim 1 wherein said process is the in vivo modulation of malignant cell development.

12. Pharmaceutical composition comprising a pharmaceutically acceptable vehicle containing at least one compound having the structure:

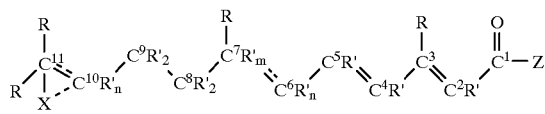

wherein:
each R is independently selected from hydrogen, or a straight chain or branched chain alkyl moiety having 1 up to 6 carbon atoms;
each R' is independently selected from hydrogen, or straight or branched chain alkyl having 1 up to 4 carbon atoms;
X is —OR", wherein R" is selected from hydrogen, a straight chain or branched chain alkyl moiety having 1 up to 6 carbon atoms, or —O—;
Z is —OR", wherein R" is as defined above;
m is 0 when there is a double bond between $C^6$ and $C^7$, or m is 1 when there is a single bond between $C^6$ and $C^7$; and
each n is 1 when there is a double bond between $C^6$ and $C^7$, and/or between $C^{10}$ and $C^{11}$, or each n is 2 when there is a single bond between $C^6$ and $C^7$, and/or between $C^{10}$ and $C^{11}$.

13. A composition according to claim 12 wherein the backbone of said compound is a 2,4-dodecadiene, each R is methyl, each R' is hydrogen, X is methoxy, Z is —OCH$_2$(CH$_3$)$_2$, m=1 and each n=2.

14. A composition according to claim 12 wherein the backbone of said compound is a 2,4-dodecadiene, each R is methyl, each R' is hydrogen, X is methoxy, Z is —OH, m=1 and each n=2.

15. A composition according to claim 12 wherein the backbone of said compound is a 2,4,6,10-dodecatetraene, each R is methyl, each R' is hydrogen, X is methoxy, Z is —OCH$_2$(CH$_3$)$_2$, m=0 and each n=1.

16. A composition according to claim 12 wherein the backbone of said compound is a 2,4,6,10-dodecatetraene, each R is methyl, each R' is hydrogen, X is methoxy, Z is —OH, m=0 and each n=1.

* * * * *